United States Patent [19]
Zelawski et al.

[11] 3,978,115
[45] Aug. 31, 1976

[54] PRECURSORS FOR PROSTAGLANDIN E$_1$

[75] Inventors: Zbigniew S. Zelawski, Piscataway; Norman L. Wendler, Summit, both of N.J.

[73] Assignee: Merck & Co., Inc., Rahway, N.J.

[22] Filed: May 14, 1975

[21] Appl. No.: 577,267

Related U.S. Application Data

[62] Division of Ser. No. 356,528, May 2, 1973.

[52] U.S. Cl. .......................... 260/488 R; 260/346.6; 260/476 R; 260/491; 260/496; 260/514 D; 260/611 R

[51] Int. Cl.² ..................... C07C 69/16; C07C 69/28

[58] Field of Search ............ 260/488 R, 410, 586 R

[56] References Cited
OTHER PUBLICATIONS

Chem. Abstracts, 50:12942h.

*Primary Examiner*—Vivian Garner
*Attorney, Agent, or Firm*—David L. Rose; Thomas E. Arther; J. Jerome Behan

[57] ABSTRACT

The disclosure relates to novel precursors for the synthesis of prostaglandin E$_1$ and the production of said precursors.

2 Claims, No Drawings

PRECURSORS FOR PROSTAGLANDIN $E_1$

This is a division of application Ser. No. 356,528, filed May 2, 1973.

BRIEF SUMMARY OF THE INVENTION

This invention relates to a new and novel synthesis of precursors of prostaglandin $E_1$ and particularly to the important intermediate 4-hydroxy-3α-methyl-1α,2α-diloweralkanoyloxymethyl cyclohexane. The synthesis involves an initial starting material already bearing a loweralkoxy functionality at one site of the eventual double bond. This invention relates further to a synthesis in which the yields are high in the several reaction steps. The invention relates still further to the novel compounds obtained as intermediates in the synthesis of the critical intermediate and to the processes for making such intermediates.

DETAILED DESCRIPTION OF THE INVENTION

Prostaglandin $E_1$, which may be depicted structurally as:

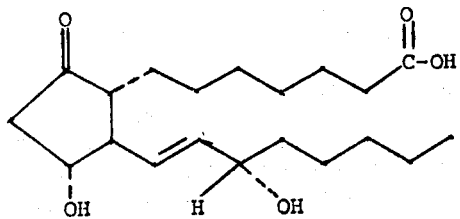

or

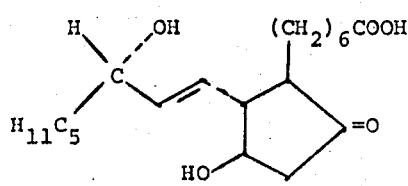

is one of a group of naturally occurring compounds known generally as prostaglandins. These prostaglandins have interesting and important biological activity, the precise biological properties varying with the individual members of the prostaglandin family, as described in the article Prostaglandins, by P. W. Ramwell et al., Progress in the Chemistry of Fats and Other Lipids, Vol. IX, Polyunsaturated Acids, Part 2, pp. 231–273, Pergamon Press (1968).

One of the more important prostaglandins is prostaglandin $E_1$, also known as $PGE_1$. It has an effect on the contractility of smooth muscle and is useful in the induction of labor in pregnant females and for the termination of pregnancy by therapeutic abortion, M. P. Embrey, British Medical Journal, 1970, 2, 256–258; 258–260. Other uses, besides stimulation of smooth muscle, are described in the literature and include lowering of blood pressure, effect on mobilization of free fatty acids from adipose tissue, inhibition of lipolysis, and bronchodilating effect.

Heretofore, the supply of prostaglandin $E_1$, as well as of other prostaglandins, has been severly limited because only minute amounts of naturally occurring material are available, and partial biosynthesis by enzymes present in mammalian seminal vesicles has only afforded limited amounts of the products.

An object of this invention is to provide a stereoselective total synthesis of a racemic precursor of ($\pm$) prostaglandin $E_1$, which compound has one-half the biological activity of the naturally occurring $PGE_1$, and an optically active precursor of ($-$) prostaglandin $E_1$, which compound has 100% of the biological activity of naturally occurring $PGE_1$ and which may be used for the same biological effects as the natural compounds.

A further object of the invention is to provide novel intermediate compounds some of which, in addition to being useful in the synthesis of ($\pm$) and ($-$) $PGE_1$, may themselves exhibit prostaglandin-like activity. An additional object is to provide a stereoselective total synthesis of other racemic or optically active members of the prostaglandin group which may be prepared by known methods from ($\pm$) and ($-$) prostaglandin $E_1$. Thus, for instance, ($\pm$) prostaglandin $F_{1\alpha}$ may be obtained by reduction of ($\pm$) $PGE_1$. Other objects will become evident from the following description of the invention.

The novel process and intermediates of our invention are shown structurally in the following flow diagram, and immediately following this diagram the chemical names of the compounds are set forth.

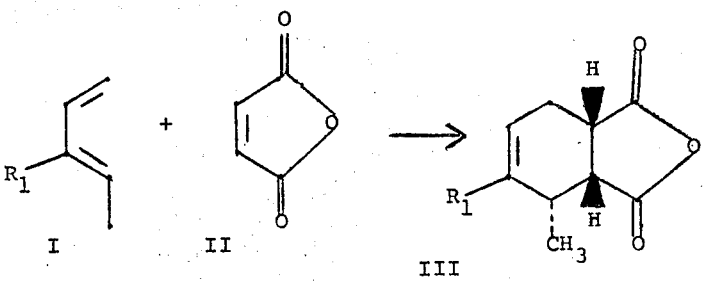

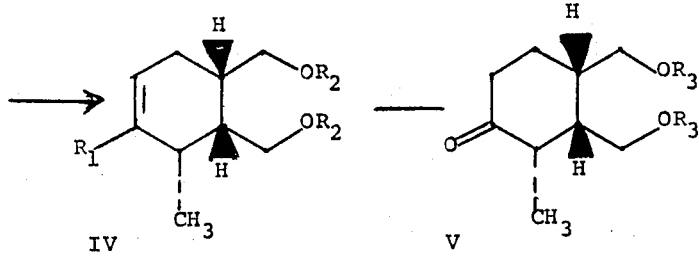

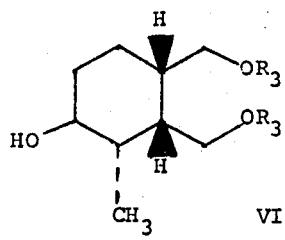

In the foregoing formulae the substituents are defined as follows:

$R_1$ = loweralkoxy
$R_2$ = hydrogen or loweralkanoyl
$R_3$ = loweralkanoyl

The loweralkyl groups of this invention are those containing from 1 to 6 carbon atoms such as methyl, ethyl, propyl, butyl, and hexyl. The loweralkoxy groups of this invention also contain 1 to 6 carbon atoms such as methoxy, ethoxy, propoxy, butoxy, and hexoxy. The loweralkanoyl groups of this invention contain from 2 to 6 carbon atoms such as acetyl, propionyl, butyryl, and hexanoyl.

As a matter of convenience for understanding the foregoing flowsheet and the following description of the invention, there follows a list of names of the chemical compounds I to VI inclusive.

I - 3-loweralkoxy-1,3-pentadiene
II - Maleic anhydride
III - 4-loweralkoxy-3α-methyl-4-cyclohexene-1α,2α-dicarboxylic acid anhydride
IV - 4-loweralkoxy-3α-methyl-1α,2α-di(hydroxymethyl)-4-cyclohexene
IV - 4-loweralkoxy-3α-methyl-1α,2α-diloweralkanoyloxymethyl-4-cyclohexene
V - 2α-methyl-3α,4α-diloweralkanoyloxymethyl cyclohexanone
VI - 4-hydroxy-3α-methyl-1α,2α-diloweralkanoyloxymethyl cyclohexane
IX - 3-methyl-1α,2α-dicyanomethyl-3-cyclohexene
X - 3-methyl-3-cyclohexene-1α,2α-diacetic acid.

In the first step of this invention a 3-loweralkoxy-1,3-pentadiene (I) is condensed with Maleic anhydride (II) in a Diels-Alder reaction to form a 4-loweralkoxy-3α-methyl-4-cyclohexene-1α,2α-dicarboxylic acid anhydride (III). The reaction is run initially at a temperature of from 20° to 40°C. but after an initial period of from 1 to 24 hours, the temperature is raised to from 50° to 100°C. for from 1 to 10 hours to complete the reaction. On cooling and removal of the solvent the product (III) is obtained which is purified using techniques known to those skilled in this art. The reaction is run in an inert solvent such as aliphatic and aromatic hydrocarbons and the like. The Diels-Alder adduct is somewhat unstable and will turn from white to yellow at 0°C. in a very few days. As a result it is beneficial if the product is used in the next synthetic step without delay.

In the next step the 4-loweralkoxy-3α-methyl-4-cyclohexene-1α,2α-dicarboxylic acid anhydride (III) is treated with a hydride reducing agent to form a 4-loweralkoxy-3α-methyl-1α,2α-di(hydroxymethyl)-4-cyclohexene (IV $R_2$=H). The hydride reducing agents such as lithium aluminum hydride, lithium borohydride are superior. The hydride reducing agents are capable of opening the anhydride ring and forming the di(hydroxymethyl) groups but will not affect any other positions of the molecule. The reaction is run in a dry inert atmosphere, such as nitrogen and in a dry solvent inert to the effects of the reducing agent. Initially the reaction is run at a temperature of from 0°C. to room temperature to prevent any rapid temperature rise due to the possible exothermicity of the reaction. When the initial reaction subsides, the reaction is heated at from 50°C. to the reflux temperature of the reaction mixture for from 1 to 6 hours. The reaction is cooled and any excess reducing agent is destroyed by the addition of a substance which will not react with the product. Generally a dilute solution of water or a loweralkanol is employed. The solvent is removed and the product (IV $R_2$=H) isolated. The material as initially isolated is generally of sufficient purity to be used without further purification in the next step.

The dihydroxy compound IV ($R_2$=H) is acylated with any of the known acylating agents. The preferred acyl group is acetyl and the preferred acylating agent is acetic anhydride. However, other acyl groups such as propionyl, benzoyl, and the like; and other acylating agents such as the corresponding acyl halide, may be used. The reaction is catalyzed by the presence of a basic catalyst, however, a preferred method is to employ a solvent which has basic characteristics in and of itself such as pyridine. The reaction is generally run substantially at room temperature for from 1 to 24 hours. When the reaction is complete, the excess acylating agent is destroyed by the addition of an inorganic base such as an alkali metal carbonate or bicarbonate and the product 4-loweralkoxy-3α-methyl-1α,2α-diloweralkanoyloxymethyl-4-cyclohexanone (IV, $R_2 = $ loweralkanoyl) isolated therefrom.

The enol ether structure of compound IV ($R_2 = $ loweralkanoyl) is removed by hydrolysis with an acid catalyst. Any mineral acid may be employed. The preferred method is to use perchloric acid as the acid catalyst. The reaction is initially cooled to from −10° to 10°C. to prevent the exothermic reaction from increasing the temperature too rapidly. When the initial exothermic reaction subsides, usually after about 10 to 30 minutes, the reaction is stirred at from 5°C. to room temperature for from 1 to 5 hours. The reaction mixture is neutralized to a pH of 6–8 and the product 2α-methyl-3α,4α-diloweralkanoyloxymethyl cyclohexanone (V) is isolated.

In the final step of this reaction sequence the keto diacetate (V) is reduced to the hydroxy compound VI.

The reduction may be affected with any of the mild reducing agents known to those skilled in this art. It is preferred, however, to use sodium borohydride. The reaction is run in a solvent, preferably one that will not be reduced by the reducing agent as a loweralkanol. Methanol has proven to give the best results. The reaction is run at from −10° to 15°C. for from 10 minutes to 2 hours. Any excess reducing agent is destroyed with a suitable reagent such as sodium dihydrogen phosphate and the product 4-hydroxy-3α-methyl-1α,2α-diloweralkanoyloxymethyl cyclohexane (VI, $R_5 = $ H) is isolated by techniques known to those skilled in this art.

The chemical procedures necessary for the preparation of prostaglandin E$_1$ from 4-hydroxy-3α-methyl-1α,2α-diloweralkanoyloxymethyl cyclohexane (VI) are set forth in our copending applications U.S. Ser. Nos. 201,959 and 201,979 filed Nov. 24, 1971, now U.S. Pat. Nos. 3,870,747 and 3,833,612, respectively.

The following examples are provided in order that the invention will be more fully understood. They should not be construed as limitative of the invention.

EXAMPLE 1

4-Ethoxy-3α-methyl-4-cyclohexene-1α,2α-dicarboxylic acid anhydride

A solution of 1.8 g. (0.016 moles) of 3-ethoxy-1,3-pentadiene in 14 ml. of benzene is added dropwise to a solution of 1.0 g. (0.010 moles) maleic anhydride in 12 ml. of benzene. The color changes from colorless to pale yellow and the temperature raises from 24° to 34.5°C. during the reaction. The reaction mixture is stirred at room temperature for 18 hours and at 80°–85°C. for 4 hours. The reaction mixture is cooled and evaporated to dryness whereupon the product precipitate as white needles melting at 96.5°–100°C. The product is dried in vacuo affording 2.05 g. of 4-ethoxy-3α-methyl-4-cyclohexene-1α,2α-dicarboxylic acid anhydride.

EXAMPLE 2

4-Ethoxy-3α-methyl-1α,2α-di(hydroxymethyl)-4-cyclohexene

A solution of 1.696 g. (0.008 moles) of 4-ethoxy-3α-methyl-4-cyclohexene-1α,2α-dicarboxylic acid anhydride in 9.5 ml. of tetrahydrofuran is added to a suspension of 0.62 g. of lithium aluminum hydride in 9.5 ml. of tetrahydrofuran. The reaction is maintained at a gentle reflux during the addition and for 3 hours thereafter. The reaction mixture is allowed to stand overnight at room temperature and the excess lithium aluminum hydride decomposed by the cautious addition of a 1:1 tetrahydrofuran water mixture. 8 Ml. of chloroform is added and the suspension filtered and the solid material washed with 3 portions of chloroform. The combined filtrates and washings are dried, evaporated to dryness, and the residue dissolved in 20 ml. of benzene, dried, and evaporated to dryness affording 1.709 g. of 4-ethoxy-3α-methyl-1α,2α-di(hydroxymethyl)-4-cyclohexene.

EXAMPLE 3

4-Ethoxy-3α-methyl-1α,2α-diacetoxymethyl-4-cyclohexene 3.0 G. of 4-ethoxy-3α-methyl-1α,2α-di(hydroxymethyl)-4-cyclohexene is combined with 3 ml. of pyridine and 5 ml. of acetic anhydride. The reaction mixture is stirred overnight at room temperature. The clear solution is then added to an excess of saturated potassium carbonate solution and stirred for 1 hour in order to decompose the excess acetic anhydride. The aqueous solution is extracted with ether and the ether extracts washed with water and 2.5N hydrochloric acid to remove traces of pyridine. The ether extracts are also washed with water and a saturated sodium chloride solution. The ether layer is dried and evaporated to dryness affording 3.78 g. of 4-ethoxy-3α-methyl-1α,2α-diacetoxymethyl-4-cyclohexene as a pale yellow oil.

EXAMPLE 4

2α-Methyl-3α,4α-diacetoxymethyl cyclohexanone 3.8 G. of 4-ethoxy-3α-methyl-1α,2α-diacetoxymethyl-4-cyclohexene is dissolved in 36 ml. of tetrahydrofuran. A 1.5M perchloric acid solution in water is added dropwise at 5°C. over a period of 15 minutes. When the addition is complete, the reaction mixture is stirred at 10°–15°C. for 2 hours. The reaction mixture is poured with vigorous stirring into a saturated aqueous potassium bicarbonate solution. The aqueous mixture is filtered, the solid material washed with tetrahydrofuran, and the filtrate concentrated to remove the tetrahydrofuran. The condensed solution is extracted with ethyl acetate and the combined extracts washed with saturated sodium chloride solution. The extracts are dried and evaporated to dryness affording 2α-methyl-3α,4α-diacetoxymethyl cyclohexanone as an orange oil weighing 3.18 g.

EXAMPLE 5

4-Hydroxy-3α-methyl-1α,2α-diacetoxymethyl cyclohexane

A solution of 3 g. (0.0117 moles) of 2α-methyl-3α,4α-diacetoxymethyl cyclohexanone in 30 ml. of methanol is added to a suspension of 0.4429 g. (0.0117 moles) of sodium borohydride in 35 ml. of methanol at 0°C. The reaction mixture is stirred at 0°C. for ½ hour. The reaction mixture is then poured into 25 ml. of water containing 3 ml. of saturated sodium dihydrogen phosphate solution. The product is extracted with ether and the combined extracts washed twice with saturated sodium chloride solution, dried, and evaporated to dryness affording 2.461 g. of 4-hydroxy-3α-methyl-1α,2α-diacetoxymethyl cyclohexane as a colorless oil.

What is claimed is:
1. 2α-Methyl-3α,4α-diloweralkanoyloxymethyl cyclohexanone.
2. The compound of claim 1 wherein the loweralkanoyloxymethyl groups are acetoxymethyl.